United States Patent [19]
Shmulewitz

[11] Patent Number: 5,782,774
[45] Date of Patent: Jul. 21, 1998

[54] APPARATUS AND METHOD OF BIOELECTRICAL IMPEDANCE ANALYSIS OF BLOOD FLOW

[75] Inventor: Ascher Shmulewitz, Mercer Island, Wash.

[73] Assignee: Imagyn Medical Technologies California, Inc., Newport Beach, Calif.

[21] Appl. No.: 726,822

[22] Filed: Oct. 4, 1996

Related U.S. Application Data

[63] Continuation-in-part of Ser. No. 634,758, Apr. 17, 1996.
[51] Int. Cl.$^6$ .................................................. A61B 5/05
[52] U.S. Cl. ........................... 600/547; 600/587; 600/481
[58] Field of Search .................................. 128/774, 282, 128/734, 671, 635, 608; 600/546, 547, 508

[56] References Cited

U.S. PATENT DOCUMENTS

| | | | |
|---|---|---|---|
| Re. 30,101 | 4/1970 | Kubicek et al. | 128/734 |
| 3,340,867 | 9/1967 | Kubicek et al. | |
| 3,651,318 | 3/1972 | Czekajewski | 235/183 |
| 3,726,269 | 4/1973 | Webster Jr. | 128/2.05 F |
| 3,915,155 | 10/1975 | Jacobson et al. | 128/2.05 F |
| 4,437,469 | 3/1984 | Djordjevich et al. | 128/672 |
| 4,450,527 | 5/1984 | Sramek | 364/415 |
| 4,671,295 | 6/1987 | Abrams et al. | 128/663 |
| 4,722,347 | 2/1988 | Abrams et al. | 128/663 |
| 4,836,214 | 6/1989 | Sramek | 128/693 |
| 4,852,580 | 8/1989 | Wood | 128/693 |
| 4,870,578 | 9/1989 | Vysin et al. | 364/413.05 |
| 4,953,556 | 9/1990 | Evans | 128/671 |
| 4,967,759 | 11/1990 | Teves | 128/715 |
| 5,005,573 | 4/1991 | Buchana | 128/207.14 |
| 5,024,228 | 6/1991 | Goldstone et al. | 128/642 |
| 5,080,107 | 1/1992 | Teves | 128/773 |
| 5,125,406 | 6/1992 | Goldstone et al. | 128/642 |
| 5,203,344 | 4/1993 | Scheltinga et al. | 128/734 |
| 5,379,765 | 1/1995 | Kaliuara et al. | 128/642 |
| 5,453,086 | 9/1995 | Weber | 604/20 |
| 5,469,859 | 11/1995 | Tsoglin et al. | 128/723 |
| 5,477,860 | 12/1995 | Essen-Moller | 128/716 |

OTHER PUBLICATIONS

"Bioelectrical Impedance Analysis in Body Composition Measurement", *National Institute of Health Technology Assessment Conference Statement*, Dec. 12–14, 1994, pp. 3–35.

"Continuous Cardiac Output Monitoring by Electrical Bioimpedance", *American College of Cardiology*, Jun. 1988, pp. 1–7.

B. Bhattacharya et al., "Potential Distribution in the Thorax in Relation to Electrical Field Plethysmography", *Medical &Biological Engineering & Computing*, May 1988, pp. 303–309.

F.H. Bonjer, M.D., et al., "The Origin of the Variations of Body Impedance Occurring During the Cardiac Cycle", *Circulation*, vol. VI, Sep. 1952, pp. 415–420.

(List continued on next page.)

*Primary Examiner*—Max Hindenburg
*Assistant Examiner*—Pamela L. Wingood
*Attorney, Agent, or Firm*—Burns, Doane, Swecker & Mathis, L.L.P.

[57] ABSTRACT

Apparatus and methods are provided for monitoring cardiac output using bioelectrical impedance techniques in which first and second electrodes are placed in the trachea and/or bronchus in the vicinity of the ascending aorta, while a sense current is injected into the thorax via first and second source electrodes, so that the resulting bioelectrical impedance measurements reflect voltage changes induced primarily by blood flow dynamics, rather than respiratory or noncardiac related physiological effects. Apparatus and methods are also provided so that the measured cardiac output may be used to control administration of intravenous fluids to a patient or to optimize heart rate for those patients having pacemakers.

24 Claims, 6 Drawing Sheets

OTHER PUBLICATIONS

David E. Clark, M.D., et al., "Thoracic Electrical Bioimpedance Measurment of Cardiac Output–Not Ready for Prime Time", *Critical Care Medicine*, vol. 21, No. 8, Aug. 1993, pp. 1111–1112.

H. Fuller, et al., "The Current Status and Future Directions of Impedance Cardiography in ICU", *Annals of Biomedical Engineering*, vol. 17, 1989, pp. 483–493.

David B. Geselowitz, "An Application of Electrocardiographic Lead Theory to Impedance Plethysomography", *IEEE Transactions on Bio–Medical Engineering*, vol. BME–18, No. 1, Jan. 1971, pp. 38–41.

Joseph C. Greenfield, Jr., M.D., et al., "Relation Between Pressure and Diameter in the Ascending Aorta of Man", *Circulation Research*, vol. X, May 1962, pp. 778–781.

Harry Handelsman, D.O., "Public Health Service Assessment Cardiac Output by Electrical Bioimpedance", *Health Technology Assessment Reports: Cardiac Output by Electrical Bioimpednace*, No. 3, 1989, pp. 1–5.

Deok W. Kim et al, "Origins of the Impedance Change in Impedance Cardiography by a Three–Dimensional Finite Element Model", *IEEE*, 1988, pp. 993–1000.

W.G. Kubicek, "On the source of Peak First Time Derivative (dZ/dt) During Impedance Cardiography", *Annals of Biomedical Engineering*, vol. 17, 1989, pp. 459–462.

John Lehr, "A Vector Derivation Useful in Impedance Plethysmographic Field Calculations", *IEEE Transactions on Biomedical Engineering*, Mar. 1972, pp. 156–157.

"Henry C. Lukaski, PhD, et al., Estimation of body Fluid Volumes Using Tetrapolar Bioelectrical Impedance Measurements", *Aviation, Space and Environmental Medicine*, Dec. 1988, pp. 1163–1169.

Daniel S. Miles, PhD et al., "Impedance Cardiography: Noninvasive Assessment of Human central Hemodynamics at Rest and During Exercise", *Exercise and Sport Sciences Reviews*, vol. 17, 1989, pp. 231–263.

Christos G. Pappas, M.D. et al., "Impedance Cardiography in the Measurement of Cardiac Output: Studies in Rabbits", *Journal of Surgical Research*, 59, 1995, pp.504–510.

R.P. Patterson, "Fundamentals of Impedance Cardiography", *IEEE Engineering in Medicine and Biology Magazine*, Mar. 1989, pp. 35–38.

Bill C. Penney, PhD., et al., "An Overview of the Theory and Some Applications of Impedance Plethysmography", *IEEE Frontiers of Engineering in Health Care*, 1981, pp.169–173.

Andrew Sherwood et al., "Committee Report; Methodological Guidelines for Impedance Cardiography", *Psychophysiology*, Feb. 1989, pp. 1–38.

William C. Shoemaker, MD, FCCM, et al., "Multicenter Trial of a New Thoracic Electrical Bioimpedance Device for Cardiac Output Estimation", *Critical Care Medicine*, vol. 22, No. 12, 1994, pp. 1907–1912.

Joseph M. VanDeWater, M.D. et al., "Developement and Evaluation of a New Impedance Cardiograph", *Journal of Clinical Engineering*, May/Jun. 1995, pp. 218–223.

Li Wang, "Contributions of Heart Movement and Blood Volume Change to Impedance Cardiography Calculated by Human Thorax Models", *IEEE*, 1993, pp. 808–809.

Li Wang, "Multiple Sources of the Impedance Cardiogram Based on 3–D Finite Difference Human Thorax Models", *IEEE*, 1995, pp. 141–148.

Klaas R. Visser, "Electrical Properties of Flowing Blood and Impedance Cardiography, *Annals of Biomedical Engineering*, vol. 17, 1989, pp. 463–473.

Xiang Wang, PhD et al., "Time–Frequency Distribution Technique in Biological Signal Processing", *Biomedical Instrumentation & Technology*, May–Jun. 1995, pp. 203–212.

APPARATUS AND METHOD OF BIOELECTRICAL IMPEDANCE ANALYSIS OF BLOOD FLOW

REFERENCE TO RELATED APPLICATION

This application is a continuation-in-part of U.S. patent application Ser. No. 08/634,758, filed Apr. 17, 1996, entitled "APPARATUS AND METHOD OF BIOELECTRICAL IMPEDANCE ANALYSIS OF BLOOD FLOW."

FIELD OF THE INVENTION

The present invention relates generally to apparatus and methods for non-invasively measuring cardiac output and, more particularly, to apparatus and methods for measuring cardiac output using bioelectrical impedance analysis techniques.

BACKGROUND OF THE INVENTION

Knowledge of cardiac output is crucial in the care of the critically ill patient, as well as patients with chronic heart disease requiring monitoring of medication. For many years the standard of cardiac output measurement has been pulmonary artery catheterization. Previously known catheterization techniques, as described, for example, in U.S. Pat. Nos. 3,915,155, 3,726,269 and 3,651,318, involve periodic injection into the patient's bloodstream of a bolus of heated saline, during which thermodilution measurements are performed to determine cardiac output. Such techniques cannot generally be used for continuous monitoring. Moreover, such catheterization techniques pose significant risk to the patient, including malignant arrhythmias, pulmonary artery rupture, and in rare cases, death.

Consequently, for many years work has been underway to develop less invasive apparatus and methods for monitoring cardiac output. For example, as an alternative to catherization methods, Doppler ultrasound techniques have been adapted to measure the velocity of blood flow. Provided that the diameter of a vessel, its flow profile, and the angle of the ultrasound beam relative to the vessel can be determined, Doppler ultrasound measurements of the ascending aorta, either externally (from the suprasternal notch) or internally (from within the trachea) can be used as a measure of cardiac output.

U.S. Pat. No. 4,671,295 describes an example of such methods and apparatus, wherein an ultrasound transducer is mounted on the tip of an endotracheal tube so that Doppler measurements of blood flow from a point (pulse wave mode) or path (continuous wave mode) along the ultrasound beam can be measured. The method described in the patent requires multiple measurements within the blood vessel, a priori knowledge of the blood flow pattern and cross-sectional area of the vessel, and the relative angulation of the blood vessel. In addition, the measurement is highly dependent upon the exact placement of the transducer. These drawbacks have resulted in the slow adoption of Doppler ultrasound cardiac output techniques.

A yet further technique which the prior art has sought to apply to the measurement of cardiac output is bioelectrical impedance analysis (BIA). BIA has recently gained wide use as a method of measuring body composition and physiological metrics. BIA involves measurement of the electrical impedance (electrical resistance plus reactance) of body tissues as a function of the voltage drop experienced by a low level alternating current (AC) electric current that is passed through the body tissues between multiple electrodes.

Generally, BIA apparatus employ two excitation electrodes between which a low level current is conducted, and two sense electrodes disposed at intermediate locations for sensing tissue impedance. Current flows predominantly through materials with high conductivities, such as blood. Less current flows through muscle, which has an intermediate conductivity, while the conductivity of fat, air and bone is much lower than that of either blood or muscle. Since the resistance to flow is a function of the conductivity and cross-sectional area of the conducting volume, volumes having a larger cross-sectional area provide lower resistance.

It is also known that the impedance of the conducting volume and the measured medium metrics (i.e., static parameters such as fat or water content, and dynamic metrics, such as blood flow) are dependent upon the placement of the electrodes and the conducting path between the electrodes. Thus, the greater the distance between the electrodes, the more likely that extraneous variables will effect the measurement.

BIA methods generally correlate the measured voltage drop between the electrodes using relatively simple algorithms based on simplified models of body structure, for example, by assuming that the body is composed of simple cylindrical resistive volumes. Temporal cyclical variations in the body impedance are then assumed to be a result of physiological events such as blood flow and breathing.

Measurements of the electrical impedance, and particularly, how the electrical impedance varies with time, can therefore provide a non-invasive indicator of those events. Various algorithms have been developed to isolate the specific physiological parameters, such as cardiac output from the measured bioelectrical impedance, as described, for example, in W. G. Kubicek, et al., "Development And Evaluation Of An Impedance Cardiac Output System," *Aerospace Medicine*, Vol. 37, pp. 1208–1212 (1966), which is incorporated herein by reference.

Despite the application of BIA methods for measuring cardiac output, no simple continuous BIA—based cardiac output measurement device has gained widespread acceptance. Many existing BIA devices use external or internal electrodes to measure bioelectrical impedance for large volumes, for example, the whole body or thoracic segments. Because the sense current diffuses throughout the entire volume, making use of any and all conductive paths, differences between individual patients, and even for the same patient over time, may inhibit standardizing the BIA metrics.

Moreover, it is known that while BIA measurements of cardiac output provide good correlation for normal patients and those hemodynamically stable patients, there is poorer correlation for critically ill patients and patients in heart failure, as described, for example, in R. J. Detemeter et al., "The Use Of Noninvasive Bioelectric Impedance To Determine Cardiac Output: Factors Affecting Its Accuracy," *Am. J. Noninvasive Cardiol.*, Vol. 2, pp. 112–118 (1988), which is incorporated herein by reference.

An example of an attempt to overcome the variabilities encountered when taking bioelectrical impedance measurements across large volumes is described, for example, in U.S. Pat. No. 4,870,578. That patent describes BIA apparatus for monitoring cardiac output by using external electrodes that measure the electrical resistance of a segment of the thorax and includes circuitry to account for large voltage changes due to respiratory-induced voltage changes. As acknowledged in that patent, the respiratory-induced voltage changes are typically much greater than the cardiac-induced voltage changes.

Other devices that attempt to account for the affect of non-cardiac physiological events on bioelectrical impedance include arranging multiple electrodes on catheters for insertion into the esophagus to measure thoracic bioelectric impedance, as described, for example, in U.S. Pat. Nos. 4,852,580 and 4,836,214. Both patents describe multi-electrode arrays inserted into the esophagus to provide an impedance measurement reflecting blood flow in the descending aorta. Such devices are not believed to provide true isolation of cardiac-induced voltage changes from those induced by other physiological events. In addition, these systems provide no mechanism for ensuring positive contact of the multiple electrodes with the wall of the esophagus.

In view of the foregoing, it would be desirable to provide apparatus and methods for accurately, non-invasively and continuously measuring cardiac output using BIA techniques.

It further would be desirable to provide apparatus and methods for measuring cardiac output in critically ill patients using BIA techniques that overcome the inaccuracies arising from measuring voltage changes across whole body or large volume thoracic segments.

It also would be desirable to provide inexpensive apparatus and methods for measuring cardiac output using BIA techniques that overcome the drawbacks of previously known BIA cardiac output measurement devices and methods.

It would further be desirable to provide methods and apparatus for continuously monitoring cardiac output so as to permit the measured cardiac output to be employed as a metric for controlling and maintaining other aspects of a patient's health.

SUMMARY OF THE INVENTION

In view of the foregoing, it is an object of this invention to provide apparatus and methods for accurately, non-invasively and continuously measuring cardiac output using BIA techniques.

It is another object of this invention to provide apparatus and methods for measuring cardiac output in critically ill patients using BIA techniques that overcome the inaccuracies arising from measuring voltage changes across the whole body or large-volume thoracic segments.

It is yet another object of the present invention to provide inexpensive apparatus and methods for measuring cardiac output using BIA techniques that overcome the drawbacks of previously known BIA cardiac output measurement devices and methods.

It is still another object of this invention to provide methods and apparatus for continuously monitoring cardiac output that permit the measured cardiac output to be employed as a metric for controlling and maintaining other aspects of a patient's health.

These and other objects of the invention are accomplished in accordance with the principles of the invention by providing BIA cardiac output monitoring apparatus that can be disposed in close relation to preferred portions of the vasculature to acquire cardiac output information. Apparatus in accordance with the present invention includes two or more sense electrodes placed in the patient's trachea and bronchus in the vicinity of the ascending aorta, and two or more source electrodes disposed on the exterior of the patient's thorax. Current conducted between the source electrodes flows throughout the thorax, and passes preferentially through blood because of the high conductivity of blood. The sense electrodes disposed in the trachea and bronchus primarily sense the impedance of blood flowing through the ascending aorta, so that voltage changes observed are due primarily to blood flow dynamics, rather than respiratory or non-cardiac related physiological effects.

Methods in accordance with the present invention overcome the inaccuracies of the gross physiologic models employed in previously known BIA cardiac methods, by avoiding the simplified algorithms for the ventricular stroke volume based on whole thorax BIA measurements. In particular, the methods of the present invention avoid the inaccuracies in whole body or thoracic BIA measurements associated with ignoring the multiple, branched and complex paths of blood flow.

In accordance with the present invention, the capability to obtain BIA measurements in the vicinity of the ascending aorta, which has no branches other than the coronary arteries, and which therefore closely reflects the flow of blood through the ascending aorta, provides a simple and highly accurate metric for computing ventricular stroke volume.

In yet further aspects of the present invention, the apparatus for monitoring a patient's cardiac output may be used to control administration of intravenous fluids to a patient or to optimize heart rate for those patients having pacemakers.

Further features of the invention, its nature and various advantages will be more apparent from the accompanying drawings and the following detailed description of the preferred embodiments.

DETAILED DESCRIPTION OF THE INVENTION

The present invention relates generally to BIA apparatus for use in measuring cardiac output in patients, including critically ill and heart-diseased patients, as well as patients undergoing elective surgery. The apparatus and methods of the present invention overcome drawbacks observed in previously known attempts to use whole body or large volume thoracic BIA measurements to measure cardiac output, by providing apparatus and methods that are not based upon the gross modeling of physiological events implicit in such previously known BIA measurement techniques.

In the exemplary embodiments of the apparatus and methods of the present invention, two or more sense electrodes are disposed on interior passageways of the body in close relation to the ascending aorta, so that voltage induced changes in bioelectrical impedance can be closely correlated to cardiac events, without significant effects due to non-cardiac physiologic events. Excitation AC current is injected into the body between two or more electrodes disposed on the exterior of the patient's thorax. Because the ascending aorta has no other branches other than the coronary arteries, flow through the ascending aorta may be closely correlated to cardiac output.

It is known in the medical literature that BIA measurements of cardiac output in general show good correlation for normal patients and hemodynamically stable patients, but much poorer correlation for critically ill patients, and patients in heart failure, as discussed in the above-mentioned Detemeter paper. Applicant has discovered that the reason for this poorer correlation in the latter cases is that the theoretical basis underlying the use of whole body or large-volume thoracic measurements may be incorrect.

While the present invention finds ready application in monitoring cardiac output in critically-ill and heart diseased patients, it may be advantageously used for all intubated patients, including pediatric cases. For example, apparatus constructed in accordance with the present invention may be readily employed in asymptomatic patients undergoing elective surgery. As many as 95% of post-operative deaths in the latter population result from hemodynamic failure.

Previously known techniques derive the equation for ventricular stroke volume (SV) from the assumption that a time-varying column of blood, in parallel with the other conducting material in the thorax, changes from zero to a volume equal to the stroke volume during the cardiac cycle. The column of blood is assumed to be the length between the electrodes used to obtain the BIA measurements, with effects on the BIA measurements due to respiration accounted for, for example, as discussed in the aforementioned U.S. Pat. No. 4,870,578.

Figure 1A:
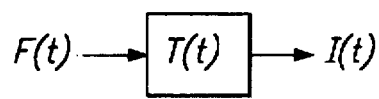
FIGS. 1A and 1B are idealized models of the volumes upon which previously known bioelectrical impedance algorithms are based.

Referring to FIG. 1A, derivation of a typical previously known BIA algorithm is illustrated. Cardiac output is estimated from the bioelectrical impedance measurement I(t), where it is assumed that changes in the bioelectrical impedance coincidental with the heart electrical activity (as represented by an electrocardiograph output) are the result of blood flow F(t). A transfer function T(t) is then based upon empirical formulae derived from measurements taken on healthy, hemodynamically stable subjects. The bioelectrical impedance is then computed as:

$$I(t)=T(t)*F(t)+N(t) \tag{1}$$

where N(t) is noise.

Applicant has determined, however, that the foregoing assumption regarding the column of blood ignores the branched, multiple and complex paths present in the arterial system. Moreover, the distribution of blood and fluids between different physiologic "compartments" in the idealized thoracic or whole body model and body regions are different in normal and critically ill patients.

Figure 1B:
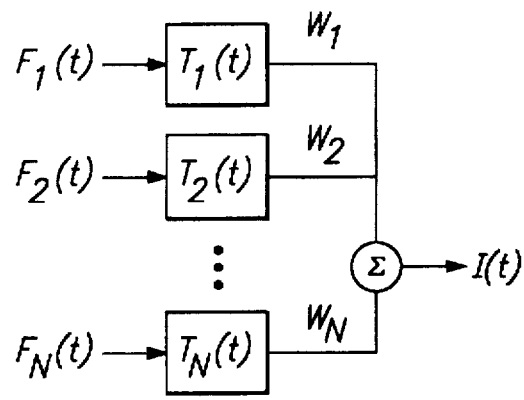

As illustrated in FIG. 1B, the thoracic approach to BIA measurement must account for transfer functions appropriate to each of the multiple blood flow paths through the volume:

$$I(t)=\Sigma F_i(t)*T_i(t)*W_i+N(t) \tag{2}$$

where Wi are weights corresponding to a priori knowledge of the relative distribution of flow through the various segments of the volume, e.g., the aorta, and arterial segments and other fluid chambers. Moreover, the weights $W_i$ may be different for different patients, may be different for chronically ill as opposed to healthy subjects, and may be variable even within a given patient, e.g., due to changes in heart rate.

Applicant has therefore discovered that equation (1) can be used accurately for any patient provided that the transfer function T(t) is correlated to measured blood flow (e.g., using a flow meter) where the effect of the distribution weights $W_i$ can be essentially eliminated. Accordingly, applicant has concluded that BIA measurements should be taken very close to a blood vessel, so that between the electrodes of the BIA apparatus there are few or no branching vessels or adjacent vessels. The present invention therefore involves the use of BIA measurements in the vicinity of blood vessels meeting the foregoing requirements.

Figure 2A:
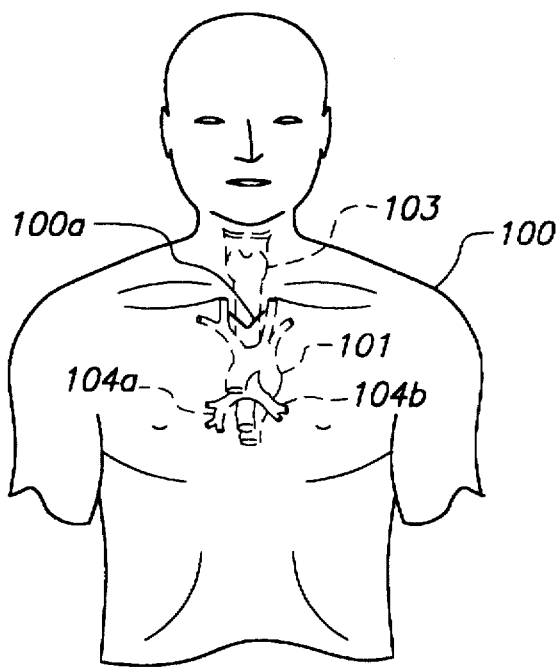
FIGS. 2A and 2B are a vertical frontal view of the upper portion of a human body and a front view of the ascending aorta, the esophagus and the trachea, respectively.

Referring to FIG. 2A, the upper portion of a human body 100 is shown in outline, with the corresponding location of the aorta 101, esophagus 102, trachea 103, and bronchi 104a and 104b, shown in dotted line. These vessels and organs are more clearly or esophagus, while source electrodes 14 are disposed on exterior 100 of the patient's thorax.

Figure 3:
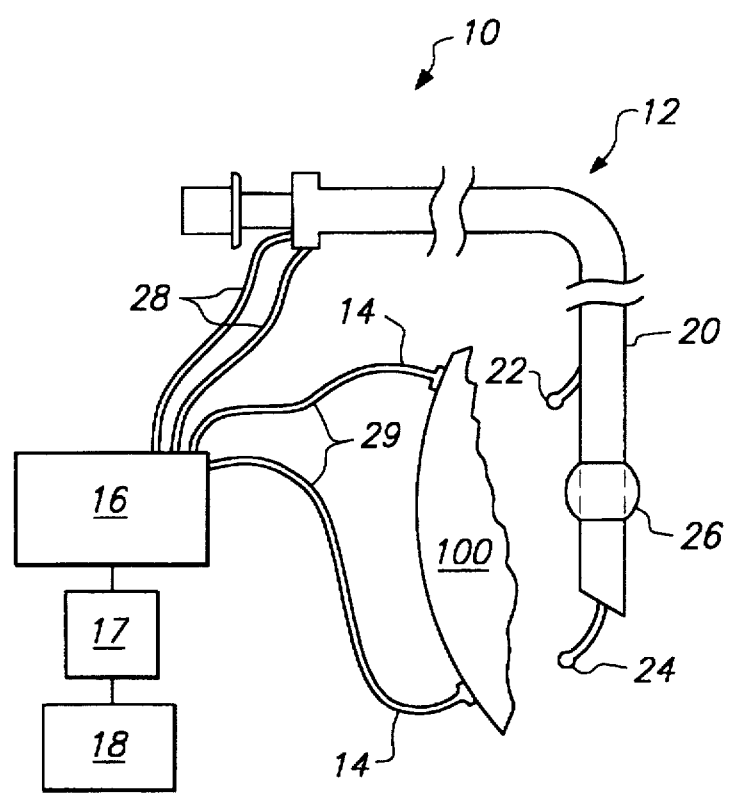
FIG. 3 is a schematic view and block diagram of a preferred embodiment of the present invention.

Sense electrode apparatus 12 comprises endotracheal tube 20 having at least one proximal sense electrode 22, at least one distal sense electrode 24, and inflatable cuff 26. Proximal sense electrode 22 is disposed in the patient's trachea at a height even with, or slightly above, the aortic arch. Distal sense electrode 24 is disposed either in the trachea near the bronchial bifurcation, or in either the right or left bronchus, at a height just adjacent to the aorta. Inflatable cuff 26 engages the interior wall of the trachea to retain endotracheal tube 20 in position. As depicted in FIG. 3, both proximal sense electrode 22 and distal sense electrode 24 comprise ellipsoidal contacts that are urged against the patient's interior passageway, and which are coupled to impedance recorder 16 via electrical leads 28.

Source electrodes 14 are placed on the exterior of the patient's thorax so as to be located outwardly of the nearest sense electrode on sense electrode apparatus 12. Thus, for example, one source electrode 14 may be disposed in the vicinity of the suprasternal notch, while a second source electrode 14 may be disposed below the xyphoid process. Source electrodes 14 are electrically coupled to impedance recorder 16 via leads 29, so that an AC sense current supplied by impedance recorder 16 flows between source electrodes 14 and the intervening tissue. Electrodes 14 may comprise spot EKG electrodes, for example, the AMI 1750-001, manufactured by Medtronic-Andover Medical, Boston, Mass.

Figure 2B:
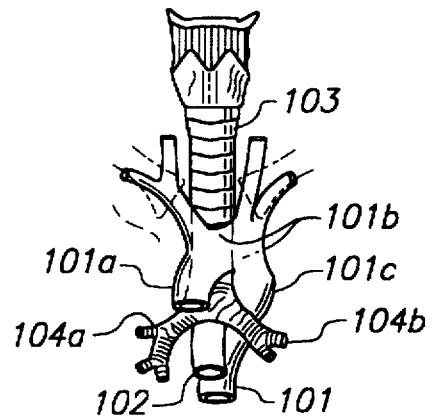

Impedance recorder 16 may be a commercially depicted in FIG. 2B. With reference to FIGS. 2A and 2B, the outflow tract of the left ventricle of the heart is the ascending aorta 101a. Segment 101b of the artery passes in front of right bronchus 104a, in front of trachea 103 and then arches 101c towards the lower part of the body behind left bronchus 104b.

Applicant has observed that because ascending aorta 101a passes in close proximity to the bronchi 104a, 104b and trachea 103, it is possible to obtain a BIA measurement across ascending aorta 101a, with relatively little intervening tissue, by disposing at least one sense electrode in trachea 103 above the aortic arch and at least another sense electrode in either the right or left bronchus, 104a and 104b, at a level just below the aortic arch. Exterior electrodes are placed on the exterior of the patient's thorax to inject an AC current into the patient's body, thereby enabling an impedance value to be sensed by the sense electrodes. Because the first branches from the aorta (other than the coronary arteries) are from aortic arch 101b, downstream of the measurement location, the measurement of blood flow from ascending aorta 101a accurately measures the volume of blood ejected from the left ventricle.

Referring now to FIG. 3, illustrative apparatus 10 constructed in accordance with the principles of the present invention is described. Apparatus 10 includes sense electrode apparatus 12, source electrodes 14, impedance recorder 16, digital sampler 17 and computer 18. As described in further detail hereinbelow, the distal region of sense electrode apparatus 12 is disposed within an internal passageway of the patient, such as the trachea, bronchi available impedance recorder providing both the sense current (generally less than 1 mA at a frequency of 50–100 kHz) and impedance measuring capability, for example, the Minnesota Impedance Cardiograph Model 304A, operating at 100 kHz. Signals output from the impedance recorder are digitally sampled by digital sampler 17, for example, at a rate of 250 Hz using a standard 12-bit analog to digital converter, available from ComputerBoards, Inc., Mansfield, Mass. The sampled output of digital sampler 17 is then provided to computer 18, for example, an IBM-compatible personal computer having an Intel 386 or higher microprocessor, for storage and processing, as described hereinbelow.

Figure 4A:
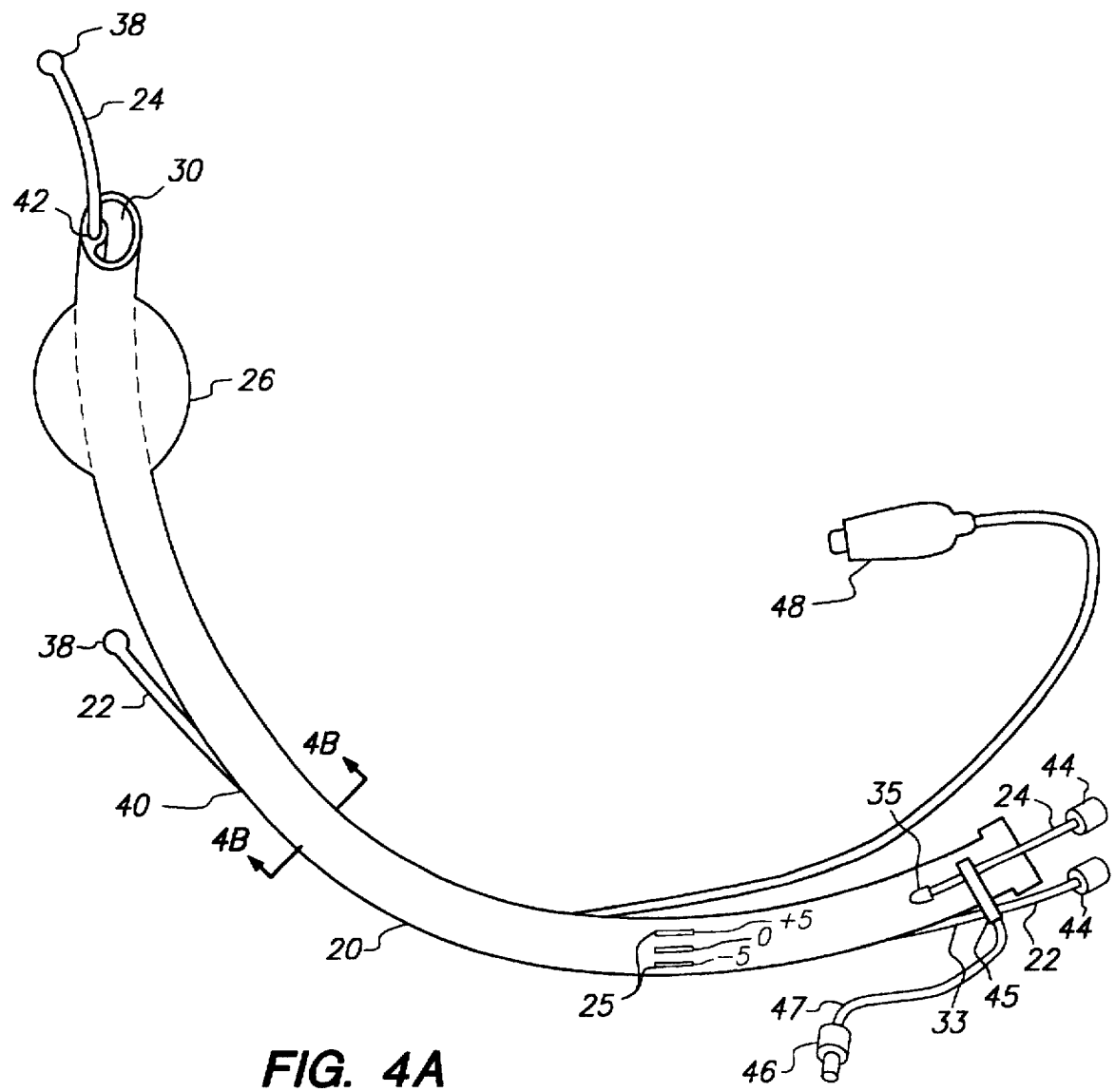
FIG. 4A is a perspective view of a first illustrative embodiment of the sense electrode apparatus of FIG. 3.
Figure 4B:
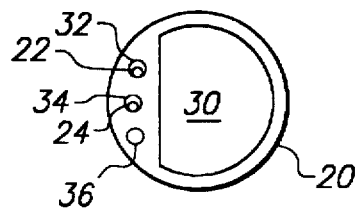
FIG. 4B is a cross-sectional view of the endotracheal tube of FIG. 4A.

Referring now to FIGS. 4A and 4B, the illustrative embodiment of sense electrode apparatus 12 of FIG. 3 is described in greater detail. Apparatus 12 comprises endotracheal tube 20 carrying proximal sense electrode 22, distal sense electrode 24, and inflatable cuff 26. As shown in FIG. 4B, endotracheal tube 20 includes lumen 30 for providing ventilation to the patient during intubation, lumen 32 through which proximal sense electrode 22 may be reciprocated, lumen 34 through which distal sense electrode 24 may be reciprocated, and lumen 36 for inflating inflatable cuff 26.

Sense electrodes 22 and 24 preferably comprise stainless steel wires about 0.020 inches thick that are pre-stressed to deflect outwardly when extended from lumen 32 and 34 of endotracheal tube 20, thus urging the electrodes into contact with the interior wall of the patient's passageways (i.e., trachea, bronchi or esophagus). Each of sense electrodes 22 and 24 preferably includes a ellipsoidal or spherical member 38 at the distal end that provides an atraumatic tip.

Sense electrode 22 enters lumen 32 through opening 33 at the proximal end of endotracheal tube 20 and exits lumen 32 through skive 40 that opens to the lateral face of endotracheal tube 20 at a location proximal to inflatable cuff 26. Sense electrode 24 enters lumen 34 through skive 35 and exits lumen 34 through outlet 42 at the distal end of endotracheal tube 20. Each of the sense electrodes preferably includes a 0.0005 inch thick layer of insulation over the length of the electrode that extends outside of lumens 32 and 34, respectively, except that ellipsoidal or spherical members 38 are bare to provide electrical connection to the interior of the patient's passageways.

Each of sense electrodes 22 and 24 includes a proximal end having positioning and locking hub 44. Each of sense electrodes 22 and 24 are disposed for sliding movement through connector block 45. Connector block 45 permits a sliding electrical connection to be established between each sense electrode and the connector block, while permitting the sense electrodes to be moved proximally and distally therethrough. Plug 46 couples sense electrodes 22 and 24 to impedance recorder 16 via cable 47 electrically connected to connector block 45.

The interior of inflatable cuff 26 is in fluid communication with insufflation port 48 via lumen 36 of endotracheal tube 20. When inflated, inflatable cuff 26 retains endotracheal tube 20 in position within the patient's interior passageway, thereby preventing inadvertent movement of endotracheal tube 20. Inflatable cuff 26 also assists in urging sense electrodes 22 and 24 into contact with the interior wall of the patient's passageways. Inflatable cuff 26 may be inflated using conventional inflation means (i.e., a liquid filled syringe or pressurized gas cylinder) connected to insufflation port 48. Alternatively, inflatable cuff 26 may be replaced by another suitable type of expandable member for urging the sense electrodes against the interior wall of the patient's passageways, such as an expanding mandrel, or other mechanical arrangement.

The proximal end of endotracheal tube 20, i.e., the end manipulated by the clinician, may include reference marks 25 on the circumference of the tube that reflect the angular orientation of electrodes 22 and 24 within the patient's trachea. The reference marks may be used to ensure proper registration of electrodes 22 and 24 with the portion of the tracheal wall and bronchus nearest to the ascending aorta.

Figure 5A:
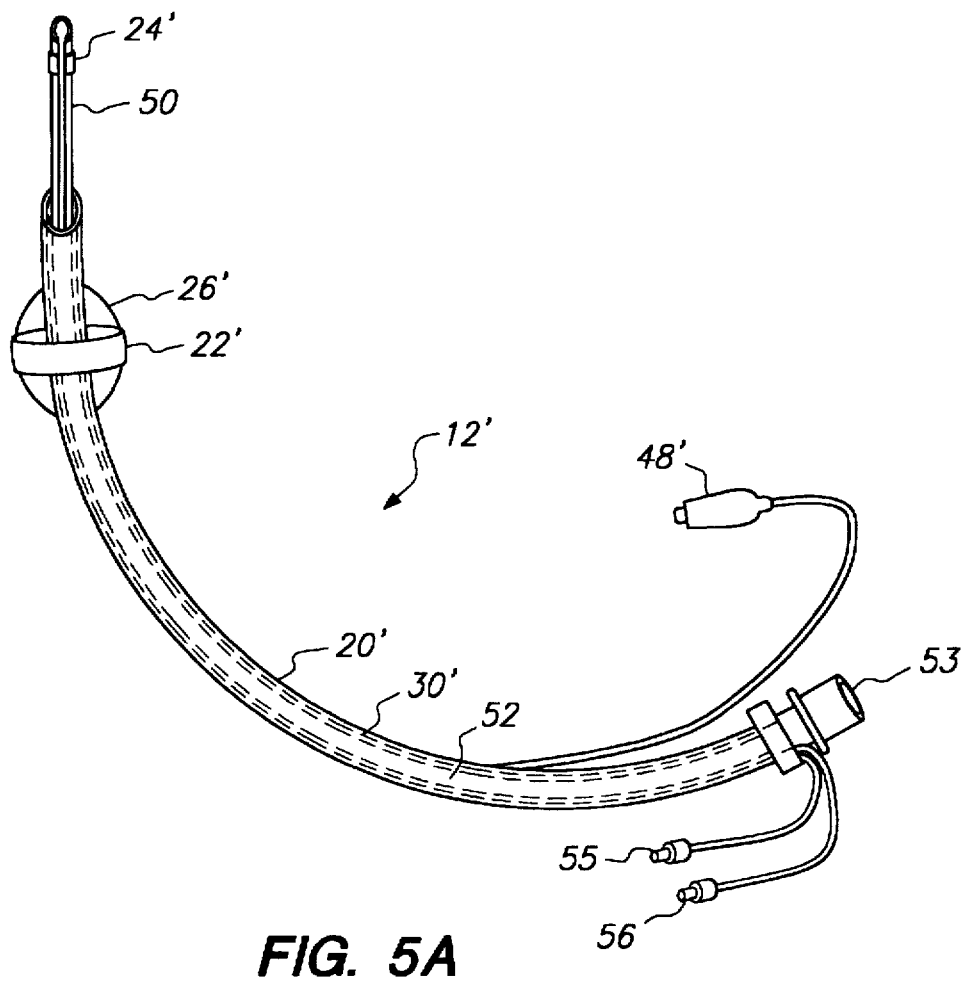
FIG. 5A is a perspective view of an alternative embodiment of sense electrode apparatus constructed in accordance with the present invention.
Figure 5B:
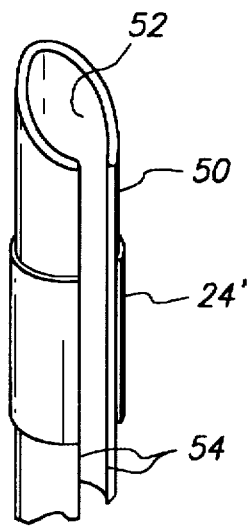
FIG. 5B is a detail view of the distal electrode of the embodiment of FIG. 5A.

Referring now to FIGS. 5A and 5B, an alternative embodiment of the sense electrode apparatus of the present invention is described. Apparatus 12' comprises endotracheal tube 20' having at least one proximal sense electrode 22' disposed upon inflatable cuff 26'. When inflated, inflatable cuff 26', which may be eccentric in shape, ensures good electrical contact between proximal sense electrode 22' and the interior of the patient's passageways. Inflatable cuff 26' may be inflated using conventional inflation means (i.e., a liquid filled syringe or pressurized gas cylinder) connected to insufflation port 48', which is in turn in fluid communication with inflatable cuff 26' through lumen 36' (not shown) extending through endotracheal tube 20'. Endotracheal tube 20' includes bore 30' within which distal electrode sheath 50 is disposed.

Expandable sheath 50 preferably comprises a compliant and resilient material, e.g., silicon tubing, and includes lumen 52 for providing ventilation to the patient via connection port 53, and for permitting the administration of oxygen during intubation. Expandable sheath 50 is disposed within bore 30' of endotracheal tube 20' so that free ends 54 of sheath 50 overlap. When extended from bore 30', expandable sheath 50 expands to urge distal sense electrode 24' against the interior of the patient's passageway (e.g., wall of the trachea or bronchus) to ensure good electrical contact therebetween. Expandable sheath 50 is slidingly disposed within bore 30' of endotracheal tube 20' so that the location of distal sense electrode 24' may be adjusted within the trachea and/or bronchus to achieve the best possible bioelectrical impedance signal.

Proximal sense electrode 22 may comprise one or more 6 mm conductive foil strips, for example, Type M6001, available from the 3M Company, St. Paul, Minn., which are electrically coupled to impedance recorder 16 via connectors 55 and electrical leads disposed within, or outside of, endotracheal tube 20'. Proximal sense electrode 22' may be disposed on the exterior of inflatable cuff 26' using a suitable adhesive or fastening means, or alternatively, may be attached directly to the exterior of the endotracheal tube 20' where inflatable cuff 26' is eccentric.

In either arrangement, inflatable cuff 26' is designed to urge proximal sense electrode 22' against the tracheal wall to ensure adequate electrical contact. Alternatively, inflatable cuff 26' may be replaced by another suitable expandable member, such as an expanding mandrel, or other mechanical arrangement.

Distal sense electrode 24' extends over the circumference of distal sheath 50, preferably between 200° and 270°, so that when distal sheath 50 is extended, electrode 24' approximates a 360° cylinder. Distal sense electrode 24' is electrically coupled via connector 56 and a lead extending within distal sheath 50.

Proximal sense electrode 22' may extend around the circumference of inflatable cuff 26' or endotracheal tube 20', or may only extend over a portion of the circumference. In addition, as for the embodiment of FIGS. 4, the proximal end of endotracheal tube 20' may include reference marks on the circumference of the tube that reflect the angular orientation of sense electrodes 22' and 24' within the patient's trachea and/or bronchus. The reference marks may then be used to ensure proper registration of sense electrodes 22' and 24' with the portion of the trachea wall and bronchus nearest to the ascending aorta.

In another alternative embodiment of sense electrode apparatus of FIGS. 5, a plurality of proximal sense electrodes 22' are disposed on endotracheal tube 20' so that the signals received from the electrodes may be optimally configured by the clinician after endotracheal tube 12' has been disposed in the patient's trachea. In addition, the extension of distal sense electrode 24 within the trachea or bronchus may also be adjusted by extending or retracting expandable sheath 50 within bore 30' of endotracheal tube 20'. In this manner, certain ones of the proximal electrodes may be selected (and the placement of distal electrode 24' adjusted) to provide an optimal output according to some predetermined metric, for example, the highest signal-to-noise ratio. In such an embodiment, impedance recorder 16 or digital sampler 17 may be modified to include suitable selection and switching logic, either as hardware or software, to select which electrodes contribute to the computed cardiac output.

Figure 6:
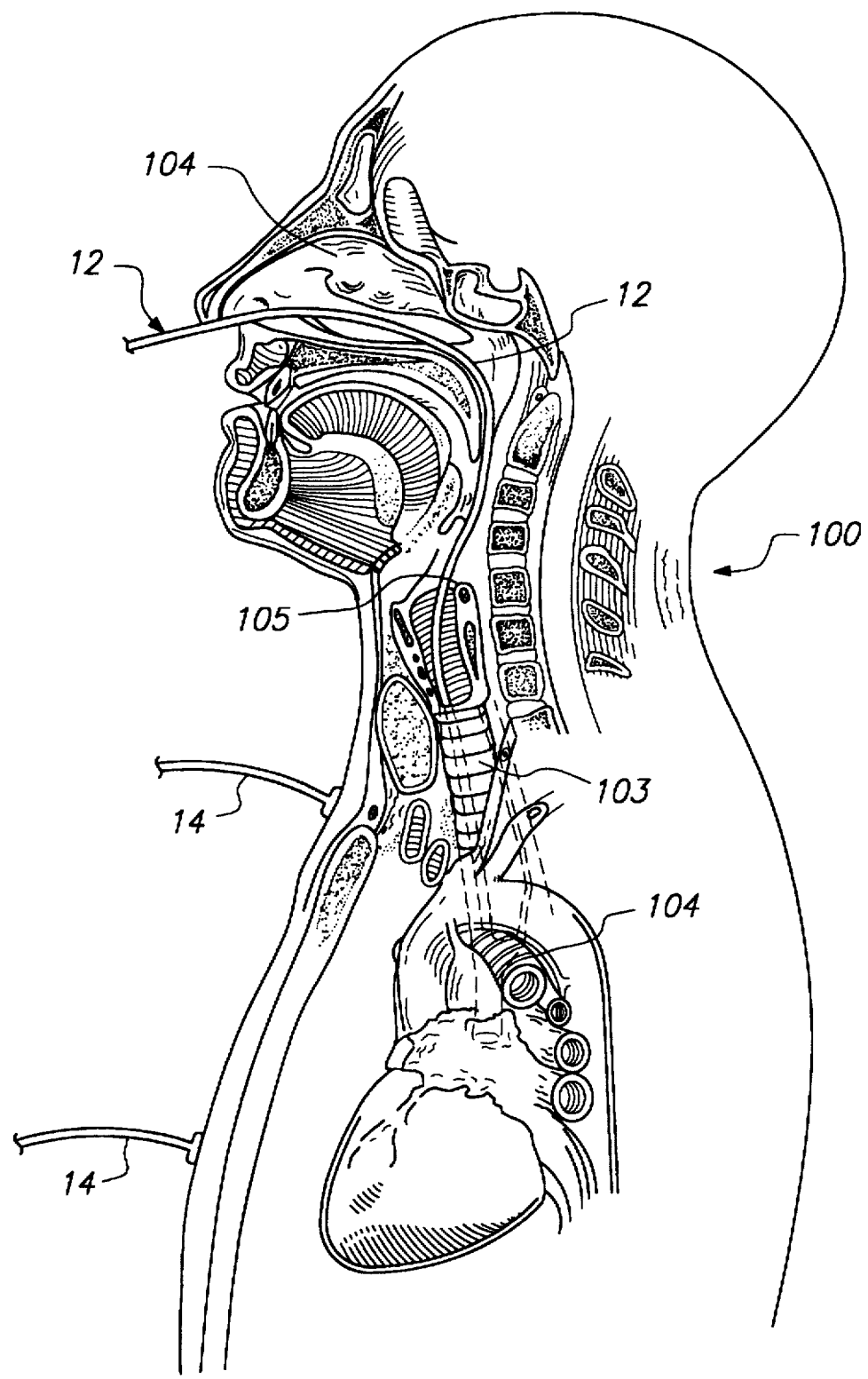
FIG. 6 is vertical cross-sectional view of the upper portion of a human body showing placement of the apparatus of the present invention.

Referring now to FIG. 6, apparatus 10 of FIG. 3 is depicted positioned within a patient. Endotracheal tube 12 is inserted into patient 100 through nasal cavity 104, past epiglottis 105 and into trachea 103 in accordance with standard intubation practice. If the apparatus of the present invention is to be used for only a relatively short period of time, e.g., while a patient is anesthetized during surgery, endotracheal tube 12 may be inserted into the trachea via the mouth. Hubs 44 of sense electrodes 22 and 24 are grasped and moved distally, thereby extending sense electrodes 22 and 24 into electrical contact with the interior of the patient's trachea and/or bronchus.

Inflatable cuff 26 is then inflated to further urge the sense electrodes into intimate electrical contact with the interior of the patient's passageways, using a suitable gas or liquid provided through the lumen in endotracheal tube 12. Alternatively, access to trachea 103 may be had through a surgical opening at the suprasternal notch 100a by conventional tracheotomy. Sense electrode apparatus 12 is connected to impedance recorder 16. Source electrodes 14 are applied to the exterior of the patient's body, preferably near the suprasternal notch and the xyphoid process, and then connected to impedance recorder 16. Bioelectrical impedance values may be then recorded for processing as described hereinbelow.

In accordance with the methods of the present invention, equations for computing cardiac output using the apparatus of the present invention are derived as follows:

The cross-sectional area, a, of a cylindrical vessel may be computed as:

$$a = (1/Z - 1/Z_0)\rho L = (\Delta Z/ZZ_0)\rho L = \Delta Z \rho L/Z^2_0 \tag{3}$$

where $Z$ is the measured electrical impedance; $Z_0$ is the baseline electrical impedance; $\rho$ is the resistivity of blood (typically 150–200 ohm-cm); L is the spacing between sense electrodes 22 and 24; and $\Delta Z = Z - Z_0$.

The instantaneous flow of blood, Q, through blood vessels of cross-sectional area a may be computed from:

$$Q = a^2 P/8\pi L \eta \tag{4}$$

where $\eta$ is the dynamic viscosity of blood, P is the average blood pressure drop along the blood vessel (a linear function of the maximum difference during the cardiac cycle) and L is the inter-electrode spacing.

Cardiac Output (CO) therefore may be computed by integrating Q over one minute intervals:

$$CO = \int Q \, dt \tag{5}$$

Applicant has observed that even in the simple parallel cylindrical model referred to in FIG. 1B, the relation between impedance changes and cardiac output is complex and dependent on the electrode configuration as well as multiple time-varying physiological parameters. Previously known bioimpedance algorithms, such as the Kubicek equation, and apparatus do not account for this complexity, and therefore have achieved limited clinical use.

In the present invention, however, the sense electrodes may be disposed in close proximity to the ascending aorta, which initial testing has shown to provide a very sharp and reproducible waveform that linearly tracks the ascending aorta blood flow wave. This linear time-varying (i.e., with cardiac cycle) relationship between blood flow and impedance change may be described as:

$$Q(t) = T(G, Z_0, t) \Delta Z(t) \tag{6}$$

where Q is the computed blood flow; T is a transfer function; G is a constant dependent upon the inter-electrode spacing and size of the electrodes; and t is the time interval relative to the cardiac cycle (e.g., the p wave of the EKG).

The transfer function T of equation (6) is empirically derived from repeated in-vivo experiments in patients with in-dwelling flow probes and continuous impedance measurements. A look-up table, LUT(t), is generated from the above-described experiments and is used to estimate the instantaneous flow Q. The Cardiac Output (CO) is then calculated based on the integral of Q over, for example, a one minute period, or by integrating the ensemble average of one cardiac cycle and multiplying by the heart rate:

$$CO = K/Z^2_0 \int LUT(t) \Delta Z(t) dt \tag{7}$$

where K is an empirically-derived constant.

Applicant expects that the BIA measurement technique in accordance with the present invention will not be significantly affected by motion artifacts or electrode placement within the trachea, so long as the electrodes are disposed so that they span the width of the aorta.

Further alternative embodiments of the present invention also may include additional sensors to enable other types of quantitative analysis. For example, diodes suitable for employing blood oximetry techniques based on near infrared light absorption also may be disposed on the endotracheal tube to measure blood oxygen saturation levels. In particular, multiple light emitting diodes, including one or more red-light and infrared emitting diodes, may be disposed on endotracheal tube 20 on inflatable cuff 26, expandable sheath 50, or both, for obtaining blood oxygen saturation measurements using transreflectance oximetry techniques, as described, for example, in U.S. Pat. No. 5,099,842, the entirety of which is incorporated herein by reference.

Figure 7A:
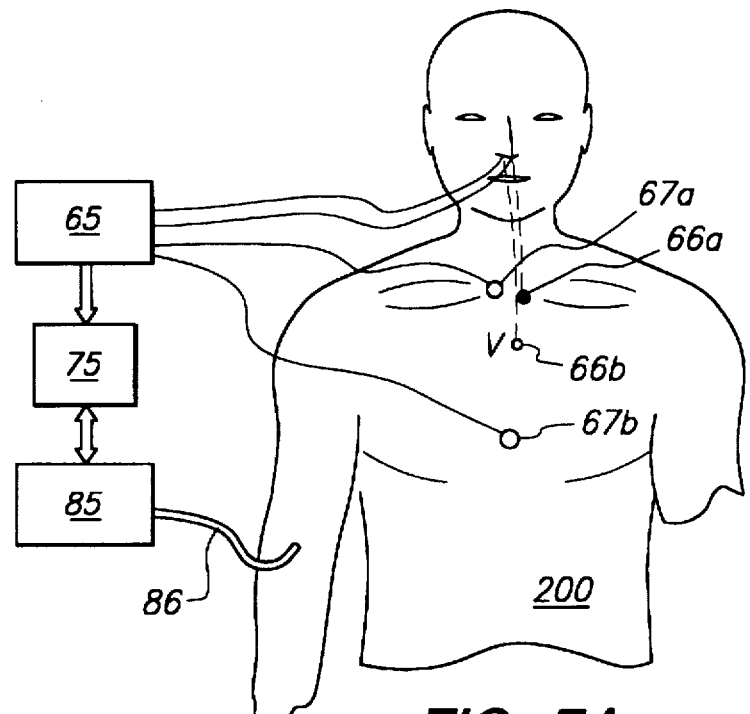
FIGS. 7A and 7B are schematic diagrams showing systems for administering fluids to a patient and for controlling heart rate for patients having pacemakers, respectively, constructed in accordance with the principles of the present invention.

Referring to FIG. 7A, an embodiment of the present invention is described as a controller for fluids administration. In FIG. 7A, cardiac output is measured by apparatus 75 having transtracheal sense electrodes 66a and 66b disposed in patient 200 on an endotracheal tube, and exterior source electrodes 67a and 67b located on the patient's chest. Apparatus 65 functions as described hereinabove with respect to the apparatus of FIG. 3, and is used to monitor hemodynamic status and as a metric to control the administration of fluids intravenously via lumen 86 coupled to fluid supply system 85. Computer 75, which may be an IBM-compatible PC (and, for example, the same computer that computes cardiac output from the measured values of bioelectrical impedance), controls fluid supply system 85.

Operation of the apparatus of FIG. 7A is as follows. After a one unit loss of blood, for example, it is known that cardiac output changes but that heart rate and blood pressure do not. Thus, decreased cardiac output can be used to monitor the amount of fluids to be given to a patient. The apparatus of FIG. 7A provides a closed-loop system wherein the amount of fluid injected into the patient is controlled by the cardiac output computed as described hereinabove. In particular, a baseline cardiac output measurement is obtained and then a bolus of 50 cc of fluid is given while cardiac output is measured continuously. As long as the cardiac output increases, additional boluses of fluid are given periodically, e.g., every 15 minutes. This process may be repeated several times a day for a critically ill patient.

Figure 7B:
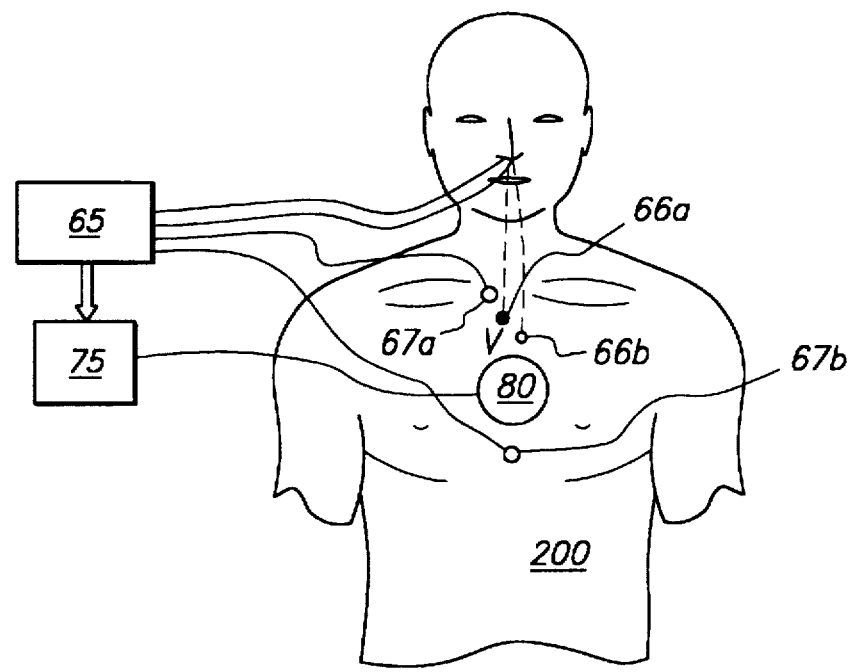

Referring now to FIG. 7B, an embodiment of the present invention is described in which apparatus 65 and computer 75 of FIG. 7A are used to control a pacemaker 80. It is desirable to maximize cardiac output for the lowest possible heart rate, since the lower the heart rate, the lower the myocardial oxygen consumption. In the arrangement of FIG. 7B, computer 75 controls the setting of pacemaker 80 as described hereinafter.

A baseline cardiac output measurement is first obtained and then the heart rate is reduced by a predetermined amount, e.g., two beats/min, while the cardiac output is continuously monitored by apparatus 65. As long as the cardiac output increases or remains unchanged, the heart rate is periodically further lowered by the predetermined amount, for example, by 2 beats/min every 15 minutes. The process of reducing heart rate while monitoring cardiac output is continued until either a minimum desired heart rate is obtained or the cardiac output measured by apparatus 65 begins to decrease. If the cardiac output is determined to have decreased, the heart rate is returned to the preceding higher rate.

Initial testing of the methods and apparatus constructed in accordance with the present invention has yielded results comparable to catheterization techniques, but with a continuous output. Animal tests have been conducted using an implanted occluder within the inferior vena cava to vary preload and a Doppler ultrasound flow probe implanted on the ascending aorta to obtain samples for correlation to the output of the bioimpedance recorder. For a population of 14 samples, correlation of the Doppler measurements to the bioimpedance measured with apparatus 20 resulted in a correlation of 0.98 with a confidence interval $p<0.005$. Initial testing in humans, for whom correlation samples were obtained using thermodilution techniques, have obtained similar results: $n=15$, $r=0.88$, $p<0.003$. In addition, no damage to tracheal mucosa has been observed, even after extended periods of intubation.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for use in combination with a bioelectrical impedance recorder and circuitry for processing the output of the bioelectrical impedance recorder to compute a metric corresponding to a patient's cardiac output, the apparatus comprising:

an endotracheal tube having a proximal portion and a distal portion;

first and second sense electrodes disposed on the distal portion and electrically coupled to the bioelectrical impedance recorder, the first and second sense electrodes spaced apart a first distance;

means for urging the first and second electrodes against a wall of the patient's interior passageway;

a reference mark disposed on the proximal portion of the endotracheal tube to determine angular orientation of the first and second sense electrodes within the patient's interior passageway, the reference mark enabling the first and second sense electrodes to be angularly aligned with the portion of interior passageway nearest the aorta;

first and second source electrodes electrically coupled to the bioelectrical impedance recorder for injecting a sense current into the patient's thorax, the first and second source electrodes spaced apart a second distance greater than the first distance, wherein the first and second sense electrodes generate a signal corresponding to the bioelectrical impedance of blood flow through the aorta and the signal is provided to the bioelectrical impedance recorder.

2. The apparatus as defined in claim 1 wherein the endotracheal tube comprises at least first and second lumens, the first and second sense electrodes comprising first and second wires disposed for sliding movement through the first and second lumens, respectively.

3. The apparatus as defined in claim 2 wherein the first and second wires include pre-stressed portions that cause the first and second sense electrodes to deflect outwardly when extended from the first and second lumens, respectively, the pre-stressed portions constituting the means for urging.

4. The apparatus as defined in claim 1 wherein the endotracheal tube further comprises an expandable member for retaining the endotracheal tube at a desired location in the passageway.

5. The apparatus as defined in claim 4 wherein the expandable member constitutes the means for urging.

6. The apparatus as defined in claim 1 wherein the endotracheal tube includes an expandable member and the first sense electrode is disposed upon the expandable member.

7. The apparatus as defined in claim 6 wherein the endotracheal tube comprises a tubular member and an expandable sheath extending from a distal tip of the tubular member, wherein the second sense electrode is disposed upon the expandable sheath.

8. The apparatus as defined in claim 7 wherein the expandable sheath is slidingly disposed within a bore of the tubular member, so that the expandable sheath may be extended into one of the bronchi of the patient.

9. The apparatus as defined in claim 8 wherein the signal may be adjusted by sliding the expandable sheath relative to the tubular member.

10. The apparatus as defined in claim 6 wherein the expandable member is an inflatable cuff, and the endotracheal tube further comprises a lumen for inflating the inflatable cuff.

11. The apparatus as defined in claim 1 wherein the endotracheal tube is adapted to be inserted in the trachea of the patient through the mouth, a nasal passageway, or a tracheotomy port.

12. The apparatus as defined in claim 1 further comprising a fluid administration system for injecting a bolus of fluid into the vascular system of the patient, the fluid administration system coupled to the circuitry for processing and responsive to the metric corresponding to the cardiac output.

13. The apparatus as defined in claim 1 further comprising a pacemaker controlling the heart rate of the patient, the pacemaker coupled to the circuitry for processing and responsive to the metric corresponding to the cardiac output.

14. A method of measuring the cardiac output of a patient comprising steps of:

providing an endotracheal tube having a proximal portion and a distal portion, first and second sense electrodes disposed on the distal portion and electrically coupled to a bioelectrical impedance recorder, means for urging the first and second electrodes against a wall of the patient's interior passageway, and a reference mark disposed on the proximal portion of the endotracheal tube to determine angular orientation of the first and second sense electrodes within an interior passageway of a patient;

positioning the endotracheal tube within an internal passageway of the patient in the vicinity of the ascending aorta so that the first and second electrodes are spaced apart a first distance;

rotating the endotracheal tube, responsive to the location of the reference mark, to adjust the angular orientation of the first and second sense electrodes within the internal passageway to a position nearest the ascending aorta;

actuating the means for urging to urge the first and second sense electrodes into electrical contact with a wall of the interior passageway;

positioning first and second source electrodes on the thorax of the patient, the first and second source electrodes spaced apart a second distance greater than the first distance;

applying a voltage between the first and second source electrodes so that a current flows through the tissues of the patient disposed along the second distance between the first and second source electrodes; and detecting with the bioelectrical impedance recorder a voltage developed across the first and second sense electrodes caused by the current flowing in the tissues of the patient, the voltage varying in accordance with changes in the bioelectrical impedance of the tissues.

15. The method as defined in claim 14 wherein the step of positioning the endotracheal tube further comprises steps of:

positioning the first sense electrode within the trachea of the patient in the vicinity of the ascending aorta; and positioning the second sense electrode within a bronchus of the patient in the vicinity of the aorta.

16. The method as defined in claim 14 wherein the step of positioning the first and second source electrodes comprises steps of:

positioning the first source electrode in the vicinity of the patient's suprasternal notch; and positioning the second source electrode in the vicinity of the patient's xyphoid process.

17. The method as defined in claim 14 wherein the step of positioning the endotracheal tube comprises a step of inserting the endotracheal tube in the trachea of the patient through a nasal passageway of the patient, the mouth of the patient, or a tracheotomy port.

18. The method as defined in claim 17 wherein the first sense electrode is disposed on the means for urging, and the means for urging comprises an inflatable cuff, the step of actuating the means for urging comprising a step of inflating the inflatable cuff.

19. The method as defined in claim 14 wherein the steps of applying a voltage between the first and second source electrodes and detecting a voltage developed across the first and second sense electrodes are performed continuously.

20. The method as defined in claim 14 further comprising steps of:

providing a fluid administration system for injecting a bolus of fluid intravenously into the patient's vascular system;

periodically actuating the fluid administration system responsive to the detected voltage developed across the first and second sense electrodes.

21. The method as defined in claim 20 wherein the step of periodically actuating the fluid administration system is performed every 15 minutes only while the cardiac output is measured to be increasing.

22. The method as defined in claim 14 further comprising steps of:

providing a pacemaker electrically coupled to the heart of the patient to control heart rate; and adjusting the heart rate responsive to voltage developed across the first and second sense electrodes to optimize cardiac output.

23. The method as defined in claim 22 wherein the step of adjusting the heart rate comprises a step of lowering the heart rate to obtain either a predetermined minimum heart rate or until the cardiac output is measured to be decreasing.

24. The method as defined in claim 23 wherein the step of lowering the heart rate comprises adjusting the heart rate downward by two beats per minute every 15 minutes.

* * * * *